(12) United States Patent
Norell

(10) Patent No.: US 8,192,702 B2
(45) Date of Patent: Jun. 5, 2012

(54) SAMPLE TUBES FOR USE IN AUTOMATED SYSTEMS AND METHODS OF MANUFACTURE

(75) Inventor: Gregory B. Norell, Morganton, NC (US)

(73) Assignee: Norell, Inc., Landisville, NJ (US)

( * ) Notice: Subject to any disclaimer, the term of this patent is extended or adjusted under 35 U.S.C. 154(b) by 2 days.

(21) Appl. No.: 12/697,740

(22) Filed: Feb. 1, 2010

(65) Prior Publication Data

US 2011/0185826 A1    Aug. 4, 2011

(51) Int. Cl.
*B01L 3/00* (2006.01)
*C03B 23/04* (2006.01)

(52) U.S. Cl. ....... 422/549; 422/550; 436/73; 435/287.1; 435/287.3; 435/288.1; 73/864.91; 414/800; 65/64

(58) Field of Classification Search .................. None
See application file for complete search history.

(56) References Cited

U.S. PATENT DOCUMENTS

| | | | |
|---|---|---|---|
| 4,923,088 A * | 5/1990 | Tanaka et al. | 220/23.87 |
| 6,812,706 B2 * | 11/2004 | Leung et al. | 324/321 |
| 6,969,993 B2 | 11/2005 | Tschirky et al. | |
| 2003/0017082 A1 * | 1/2003 | van Deursen et al. | 422/102 |
| 2005/0062474 A1 * | 3/2005 | Tschirky et al. | 324/321 |
| 2010/0043572 A1 * | 2/2010 | Himmelsbach et al. | 73/863.11 |

* cited by examiner

*Primary Examiner* — In Suk Bullock
*Assistant Examiner* — Timothy G Kingan
(74) *Attorney, Agent, or Firm* — Diehl Sevilla LLC; Jeffrey I. Blankman

(57) ABSTRACT

One or more embodiments of the invention are directed to sample tubes comprising a cylindrical elongate tube having a gripping section with at least one discontinuity extending radially about the outside surface of the elongate tube. Methods of making sample tubes and their use in sample handlers are also described.

16 Claims, 9 Drawing Sheets

A   B   C   D

E   F   G   H

SAMPLE TUBES FOR USE IN AUTOMATED SYSTEMS AND METHODS OF MANUFACTURE

TECHNICAL FIELD

Embodiments of the invention are directed to sample tubes for use with automated systems. More specifically, embodiments of the invention are directed to sample tubes having grooves or ribs for using with robotic or automated sample handling systems, and more particularly, with Nuclear Magnetic Resonance (NMR) spectrometry instruments and the like.

BACKGROUND

Nuclear magnetic resonance (NMR) spectroscopy and electron paramagnetic resonance (EPR) are widely used techniques, amongst others, in physical and biological science for structural analysis of compounds. Generally, an aliquot of solution in an elongate precision-made sample tube is placed in a sample chamber located between poles of a powerful magnet and subjected to radio frequency excitation. The sample tube is customarily axially rotated to average out the magnetic field and radio frequency excitation.

Sample tubes for the instruments are frequently made of glass and are available in a plurality of diameters generally ranging from about 0.5 mm to about 16 mm with lengths ranging from about 100 mm to about 8 inches. The most widely used tubes are about 5 mm in diameter and about 7-8 inches long. In use, the tubes are placed in a tube holder that is specifically designed to fit a particular manufacturer's instrument. The tube holder is a precision-made air turbine that spins the sample during the determination of the spectrum.

Since the tubes are elongate and spun during the determination of the spectrum, it is important that the tubes are substantially straight and are substantially coaxial with the tube holder. If the tubes are not substantially straight and coaxial with the tube holder, when the tubes are spun, there will be substantial "run-out" of the bottom portion of the tube that is between the excitation coils and the poles of the magnet. This run-out will degrade the resolution of the spectrum and is very undesirable.

Instrumentation manufacturers supply tube holders to fit specific size tubes. These tube holders, since they are precision-made air turbines, are costly and most users only inventory tube holders for the most commonly used size tubes. In many instances, researchers may only have small amounts of a compound available for testing. In these cases, the standard 5 mm/8 inch tube does not provide a satisfactory vessel for evaluation of these small amounts. As a result, tube manufacturers have developed several sample tubes and adapters to enable use of smaller diameter/low volume samples in standard sample holders.

Laboratory automation systems are frequently used for automated sample preparation and high-throughput screening. Many automated systems require the use of specially shaped tube caps which can be gripped and moved. A particular difficulty with these systems is that the cap can be separated from the sample tube by the autosampler.

Accordingly, there is a need for more universally applicable and simple to use sample tubes capable of being employed in automated sample preparation and analysis systems.

SUMMARY

This application is generally related to sample tubes that are picked, filled with sample and placed into an instrument for measurement of a property of the sample using robotic or automated sample handling systems, and more particularly, to a Nuclear Magnetic Resonance (NMR) spectrometry sample tube or container.

One or more aspects of the invention are directed to sample tubes comprising a cylindrical elongate tube having an inside surface, an outside surface, an open end, a closed end and a gripping section adjacent the open end. The gripping section has at least one discontinuity extending about the outside surface of the elongate tube.

In some embodiments, the at least one discontinuity is one or more of a projection and a recess. In detailed embodiments, there are two discontinuities in the gripping section of the elongate tube. In more detailed embodiments, there are three discontinuities in the gripping section of the elongate tube.

The elongate tube of some embodiments is constructed from a material selected from the group consisting of borosilicate glass, soda lime glass, flint glass, polytetrafluoroethylene (PTFE), fluorinated ethylene-propylene (FEP) polymer and perfluoroalkoxy (PFA) polymer.

The gripping section of detailed embodiments is integrally formed with the cylindrical elongate tube. The gripping section of some embodiments comprises a sleeve not integrally formed with the elongate tube.

The sample tube of some embodiments has an elongate tube with a diameter in the range of about 0.77 mm to about 25 mm. In detailed embodiments, the gripping section has a larger outer diameter than the elongate tube. In some embodiments, the gripping section has a smaller outer diameter than the elongate tube. The sample tube of detailed embodiments has a length in the range of about 4 inches to about 16 inches.

In some embodiments, the closed end of the cylindrical elongate tube is integrally formed with the elongate tube. In detailed embodiments, the closed end of the cylindrical elongate tube comprises a plug not integrally formed with the elongate tube. According to specific embodiments, the plug forms a fluid tight seal with the inside surface of the elongate tube by one or more of a friction fit, heat fusing or an adhesive.

One or more embodiments have the at least one discontinuity in the gripping section formed by one or more of molding, tooling and machining processes.

Additional aspects of the invention are directed to methods of making sample tubes. A cylindrical elongate tube is formed having an inside surface, an outside surface and two ends. A first end of the cylindrical elongate tube is closed to form a tube having a closed first end and an open second end. At least one discontinuity is formed along a gripping region located adjacent the open second end of the tube.

In detailed embodiments, the elongate tube, closed first end and the at least one discontinuity are formed substantially simultaneously. In some embodiments, the closed first end of the elongate tube is closed by one or more of heat sealing or plugging the first end of the elongate tube.

According to some embodiments, the at least one discontinuity is formed by a machining process. In various embodiments, the at least one discontinuity is formed by tooling the second open end of the elongate tube using a discontinuity tool. In specific embodiments, the discontinuity tool comprises a pin for tooling the inner surface of the elongate tube and at least one jaw for tooling the outside surface of the elongate tube.

Further aspects of the invention are directed to methods of using a sample tube in a sample handler, where the sample tube has an open end, a closed end and one or more discontinuities near the open end. The closed end of the sample tube is placed in a holder in the sample handler. A gripping device moves to the open end of the sample tube so that the gripping device cooperatively interacts with the one or more discontinuities in the sample tube. The gripping devices and the sample tube are lifted out of the sample handler.

Detailed embodiments include capping of the open end of the sample tube.

DETAILED DESCRIPTION

Figure 1:
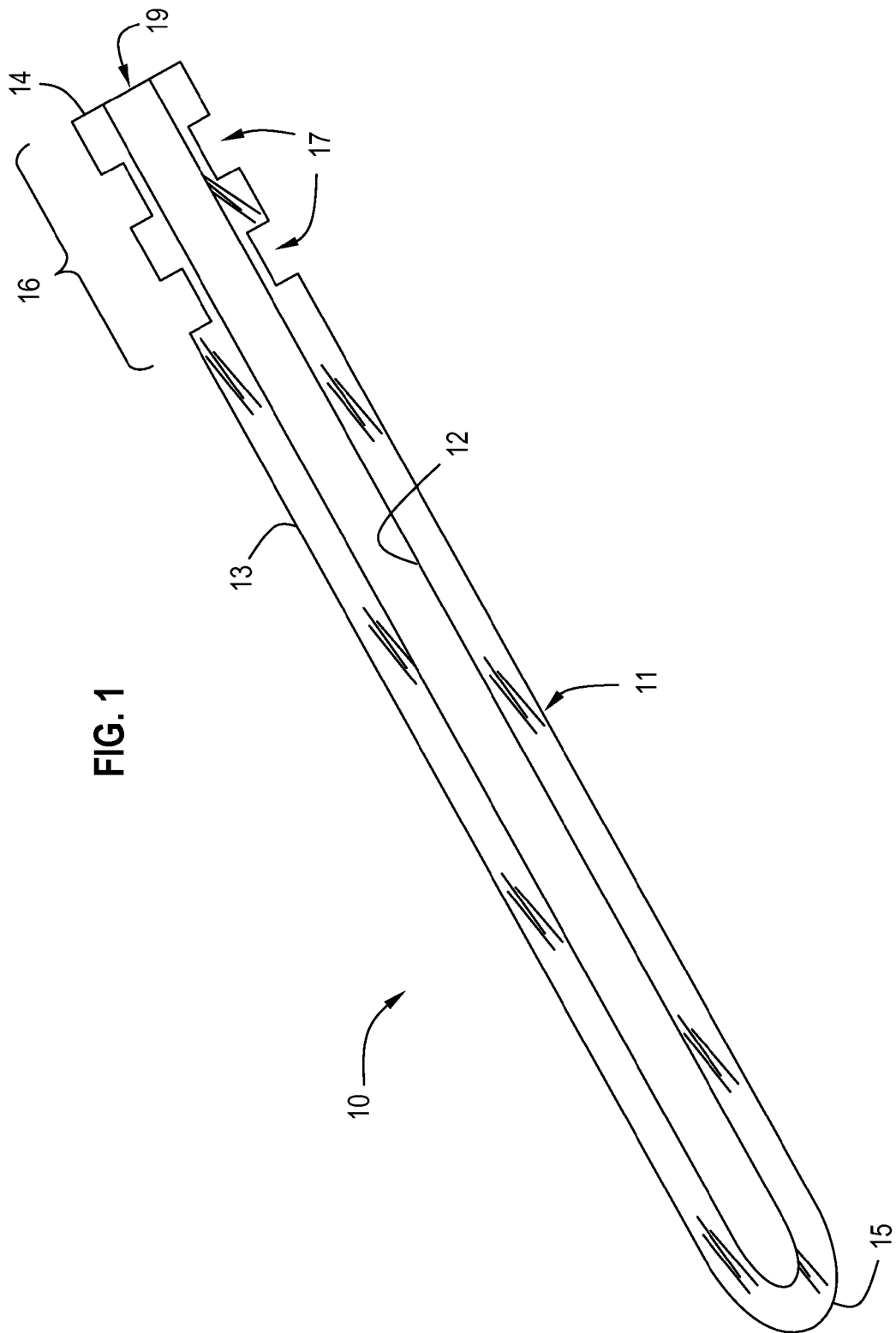
FIG. 1 shows a cross-sectional view of a sample tube in accordance with an aspect of the present invention.

Before describing several exemplary embodiments of the invention, it is to be understood that the invention is not limited to the details of construction or process steps set forth in the following description. The invention is capable of other embodiments and of being practiced or being carried out in various ways.

As used in this specification and the appended claims, the terms "discontinuity" and "discontinuities" refers to a surface feature which results in a recess or a projection, or combinations thereof, such as a groove or rib.

As used in this specification and the appended claims, the terms "recess" and "groove" are used interchangeably. Additionally, the terms "projection" and "rib" are used interchangeably.

Automated sample handling systems sometimes employ a set of fingers or rounded grippers that open and close onto the outside surface of a sample container. Automated systems that employ robotic fingers usually make a point contact on the sample container, whereas the robotic systems using rounded grippers usually make a line contact, either circumferentially or axially on the outside surface of the sample container.

By placing a recess (or groove) on the outside surface of the sample tube where the robotic fingers make contact, the fingers can maintain a positive grip, limiting movement or slippage of the tube in the fingers. This can be important when accurate depth or height placement is necessary. If the recess (groove) is formed accurately, i.e., the width and depth of the groove is dimensionally consistent around the circumference of the tube and the groove is closely oriented at a 90 degree angle to the longitudinal axis of the tube, a high degree of axial alignment with respect to the robotic arm movement (usually referred to as "Z"-axis movement) can be realized. This can be important when the automated system must place the tube accurately, for instance, into a small hole of a tube rack or into a holder such as a spinner turbine.

For the automated systems using rounded robotic grippers, two projections (or ribs) can be fashioned circumferentially onto the outside perimeter of the sample tube. One rib can be placed above the contact area of the grippers, and a second rib can be placed below the contact area of the grippers, thereby limiting movement or slippage of the tube in the grippers.

Limiting slippage of the tube in the rounded robotic grippers is important for the same reasons as described for the robotic fingers, namely, to maintain accurate depth or height placement. Rounded robotic grippers, because of their shape, can inherently grip and axially align the tube accurately with respect to the "Z"-axis movement of the robotic arm. However, this is true only when the outside diameter of the sample tube closely matches the diameter (or radius of curvature) of the inside surface of the rounded grippers. For example, a smaller outside diameter tube can experience increased lateral or sideways movement in the rounded grippers because of the mismatch of the tube diameter to the nominal design diameter of the rounded grippers. To this end, the outside diameter of a smaller sample tube can be increased throughout the area of contact of the rounded grippers (i.e., between the two ribs) to match the nominal design diameter of the rounded grippers.

Though robotic fingers can usually accommodate a wider range of sample tube diameters, because of their design, than rounded robotic grippers, it is also sometimes desirable or necessary to match the outside diameter of the sample tube at the point of contact of the robotic fingers to the nominal design diameter of the fingers. This is especially true for much smaller or much larger diameter sample tubes.

Both robotic systems, fingers and rounded grippers alike, are limited to a maximum tube diameter. When the outside diameter of the sample tube exceeds this maximum capacity, the diameter of the sample tube can be reduced throughout the area of contact of the robotic fingers or rounded robotic grippers, whichever may be the case, to match the nominal design diameter of the fingers or rounded grippers.

Enlarging or reducing the diameter of the sample tube in the area of contact of the robotic fingers or rounded robotic grippers can be accomplished using the same methods employed for fashioning the ribs onto the outside surface of the sample tube, namely, molding, tooling or machining.

Accordingly, with reference to FIG. 1, one or more embodiments of the invention are directed to sample tubes 10 comprising a cylindrical elongate tube 11 having an inside surface 12, an outside surface 13, an open end 14 and a closed end 15. The sample tube 10 includes a gripping section 16 located adjacent to the open end 14. The gripping section 16 has at least one discontinuity 17 extending radially about the outside surface 13 of the elongate tube 11. The length of the gripping section 16 can be changed depending on the desired configuration of the sample tube 10 and should not be considered to limit the scope of the invention.

In some detailed embodiments, the open end 14 of the sample tube 10 has a opening 19. The opening 19 allows for the introduction of sample into the sample tube 10. The opening 19 can be left open during use or closed with a suitable closure (not shown). Non-limiting examples of suitable closures include a cap which fits into the opening 19 and a cap which fits over the open end 14 of the sample tube 10. In specific embodiments, the cap includes a lip which, when placed on the open end 14, extends along the gripping region 16 of the sample tube 10. The gripping region 16, adjacent the open end 14, can include a projection (e.g., a rolled edge) which the cap can cooperatively interact with to seal the sample within the tube. In some embodiments, the cap includes a region suitable for piercing, such as a septum, to allow a sample to be injected through the cap into the sample tube 10.

Figure 2:
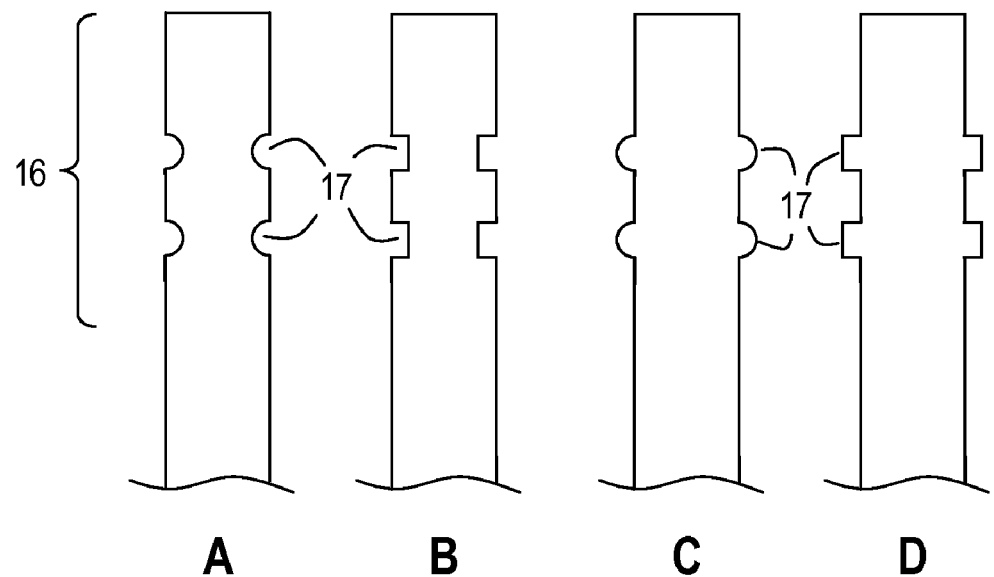
FIG. 2 shows cross-sectional views of end sections of sample tubes in accordance with one or more embodiments of the present invention.
Figure 2:
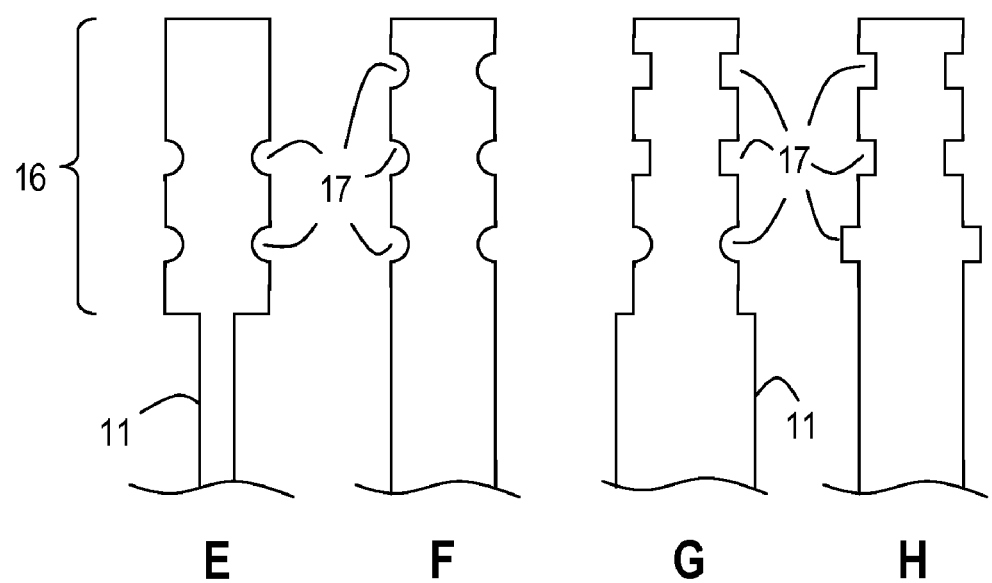

Without being limited to the configurations shown, FIG. 2 includes partial cross-sections of discontinuities in accordance with various embodiments of the invention. Near the open end 14 of the sample tube 10, there are one, two or more discontinuities (grooves and/or ribs) formed or placed onto the outside perimeter of the tube by molding, tooling or machining. The grooves and/or ribs are intended to facilitate handling of the sample tubes by automated systems. In detailed embodiments, the discontinuity 17 is one or more of a recess (see FIG. 2A) and a projection (see FIG. 2C).

In one or more embodiments, the diameter of the gripping region 16 is sized to cooperatively interact with a laboratory automation system. As used in this specification and the appended claims, the term "cooperatively interact with a laboratory automation system" means that the gripping region 16 and discontinuities 17 are sized to match the nominal design diameter of the robotic fingers, rounded grippers, etc., used in automated sample handling systems.

In specific embodiments, there are two discontinuities 17 in the gripping section 16 of the elongate tube 11. (See FIG. 2A-2E) In more specific embodiments, there are three discontinuities 17 in the gripping section 16 of the elongate tube 11. (See FIGS. 2F-2H) The type of discontinuity can be varied and mixed. For example, FIG. 2G shows a tube 11 having three discontinuities 17, where one is semicircular and two are rectangular. Another example shown in FIG. 2H has three discontinuities 17 where two are recesses and one is a projection. By combining different types and sizes of discontinuities 17 a sample tube can be made to be compatible with multiple automation systems, allowing the sample tube to be exchanged between a combination of otherwise incompatible instruments. In specific embodiments, the discontinuities 17 in the gripping section 16 are formed by one or more of molding, tooling and machining processes.

Figure 2I:
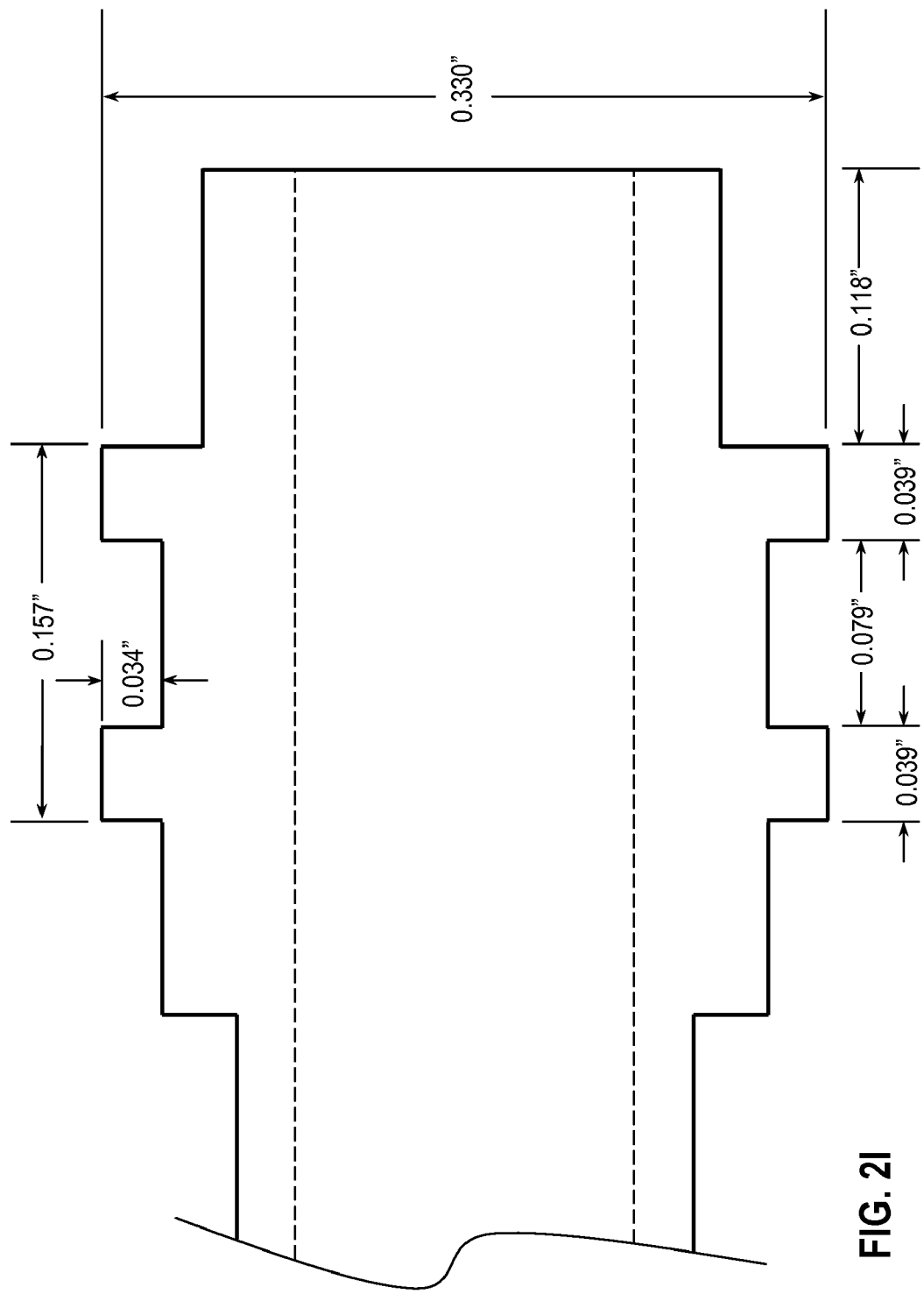

One specific embodiment suitable for use with the Bruker SampleJet system, shown in FIG. 2I, has two rectangular projections. The outside diameter of both projections is about 0.330 inch (about 8.38 mm); the width of each projection is about 0.039 inch (about 1.0 mm). The rectangular recess so formed between the adjoining projections has a width of about 0.079 inch (about 2.0 mm) and a depth of about 0.034 inch (about 0.86 mm). The shoulder or edge of the first projection is about 0.118 inch (about 3.0 mm) from the open end of the elongate tube. The discontinuities (two projections and an intervening recess) span a length of about 0.157 inch (about 4.0 mm). Measurements not provided are variable depending on the specific sample tube. Each dimension is an approximation, and small variations are tolerated and expected.

Figure 2J:
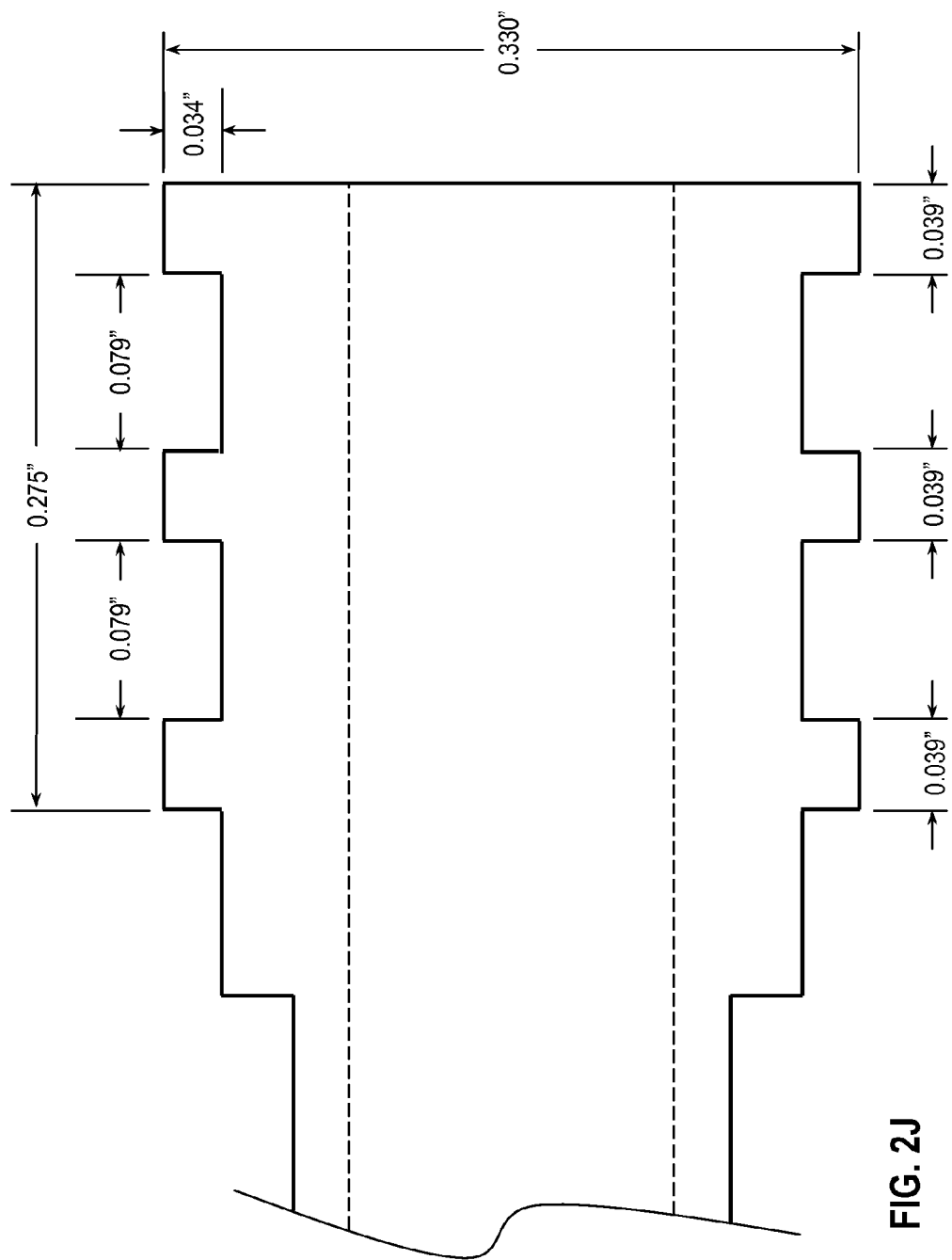

In another specific embodiment, which may be suitable for future use in the Bruker SampleJet system, three rectangular projections are present, as shown in FIG. 2J. The two lower projections and the intervening recess are identical in all respects to those described in the preceding paragraph. The shoulder or edge of the third additional projection is located immediately adjacent to the open end of the elongate tube. This projection also has an outside diameter of about 0.330 inch (about 8.38 mm) and a width of about 0.039 inch (about 1.0 mm). The adjacent rectangular recess thus created has a width of about 0.079 inch (about 2.0 mm) and a depth of about 0.073 inch (about 1.85 mm). The discontinuities (three projections and two intervening recesses) span a length of about 0.275 inch (about 7.0 mm). Measurements not provided are variable depending on the specific sample tube. Each dimension is an approximation, and small variations are tolerated and expected.

Figure 2K:
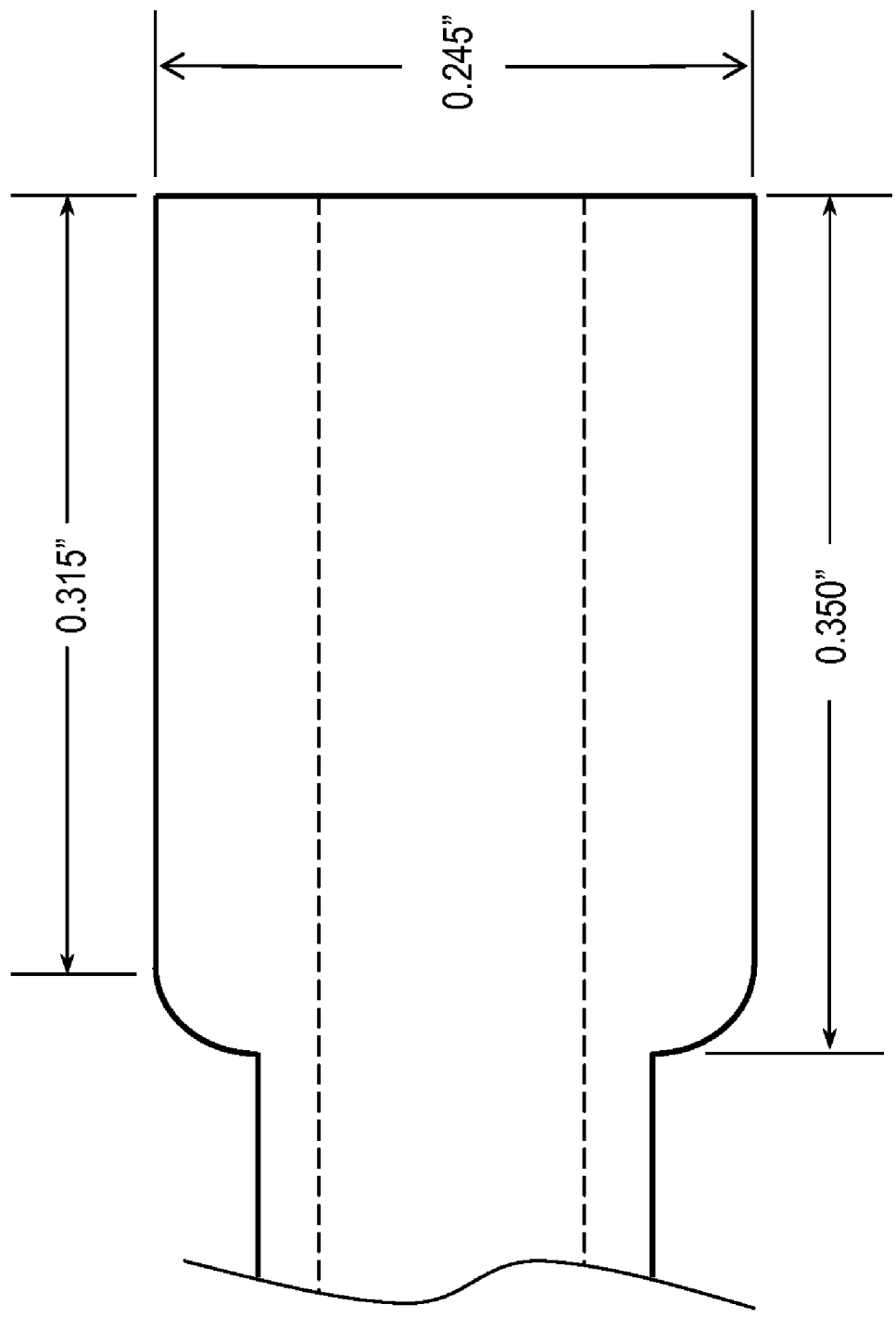

A third specific embodiment, which is suitable for use with the Varian 768AS autosampler system, incorporates one projection with a rounded lower shoulder portion as shown in FIG. 2K. The projection is situated immediately adjacent to the open end of the elongate tube, and as such, there is no upper shoulder portion because the inside diameter of the projection also forms the open end of the elongate tube. This projection has an outside diameter of about 0.245 inch (about 6.2 mm) and a length of about 0.315 inch (about 8.0 mm). The discontinuity (the projection and its rounded shoulder portion) span a length of about 0.350 inch (about 8.9 mm). This embodiment meets fully the design criteria of the Varian 768AS autosampler system. Measurements not provided are variable depending on the specific sample tube. Each dimension is an approximation, and small variations are tolerated and expected.

A fourth specific embodiment (not shown), also suitable for use with the Varian 768AS autosampler system, incorporates three projections. The additional two projections are designed to limit slippage of the tube in the rounded robotic grippers used on the Varian 768AS system These two outer rounded projections, shorter in length but with larger outside diameters are placed on either side of the central projection. The central projection, with two rounded shoulders, has the same outside diameter of about 0.245 inch (about 6.2 mm) and the same length of about 0.315 inch (about 8.0 mm) as described in the preceding paragraph. The outer two adjoining projections each have outside diameters of about 0.323 inch (about 8.2 mm) and are about 0.063 inch (about 1.6 mm) long, each separated from the central projection by a space of about 0.063 inch (about 1.6 mm). The topmost outer projection is placed immediately adjacent to the open end of the elongate tube. The discontinuities (three projections and the rounded shoulder portions) span a length of about 0.565 inch (about 14.35 mm). Each dimension is an approximation, and small variations are tolerated.

Figure 3:
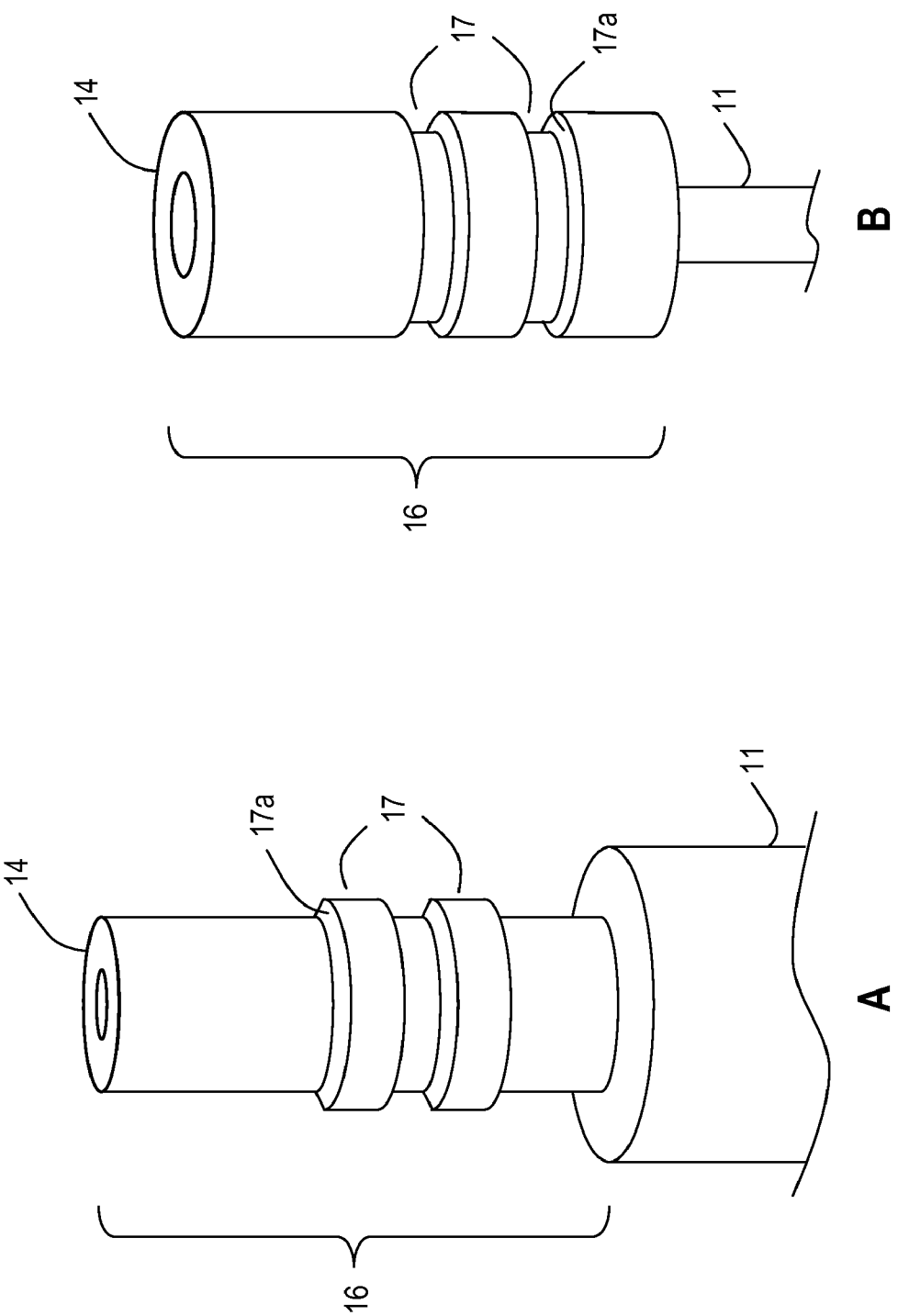
FIG. 3 shows perspective views of end sections of sample tubes in accordance with one or more embodiments of the present invention.

FIG. 3A shows a specific embodiment of the invention. The gripping region 16 is roughly defined as extending from the open end 14 of the sample tube 10 to the elongate tube 11 portion. The gripping region 16 is shown with two discontinuities 17 as projections from the gripping region 16. The elongate tube 11 portion of the sample tube 10 has a larger outer diameter than the gripping region 16. The shoulder portions 17*a* of the discontinuities 17 can be perpendicular to the sample tube 10 axis, or at various angles to the sample tube 10 axis. The embodiment shown in FIG. 3A is merely representative and should not be taken as limiting the scope of the invention.

FIG. 3B shows another specific embodiment of the invention. The gripping region 16 extends roughly from the open end 14 of the sample tube 10 to the elongate tube 11 portion. Here, the gripping region 16 has two discontinuities 17, shown as rectangular shaped recesses. The elongate tube 11 portion of the sample tube 10 has a smaller outer diameter than the gripping regions 16. The shoulder portions 17*a* of the discontinuities 17 can be perpendicular to the sample tube 10 axis, or at various angles to the sample tube 10 axis. The embodiment shown in FIG. 3B is merely representative and should not be taken as limiting the scope of the invention. This embodiment also shows an example of a gripping region 16 that has not been formed as an integral part of the sample tube 10, but rather has been formed as a separate piece in the form of a sleeve or hollow tube that fits closely over the outside diameter of the elongate tube 11. This sleeve can then be secured in place by, for example, fusing it to the elongate tube with heat, by a friction or press fit, or by means of an adhesive bonding material.

The sample tubes 10 are usually comprised of borosilicate glass of ASTM Type 1 Class A or ASTM Type 1 Class B. However, sample tubes 10 can also be made from what is commonly known as soda lime glass or flint glass; or a fluorinated polymeric material such as polytetrafluoroethylene (PTFE), fluorinated ethylene-propylene (FEP) polymer or perfluoroalkoxy (PFA) polymer. In specific embodiments, the gripping section 16 is integrally formed with the cylindrical elongate tube 11. For example, the gripping section 16 and elongate tube 11 are made of a continuous piece of material. In specific embodiments, the sample tube 10 is made of an amber material to provide protection for light sensitive samples. Other materials can be used in accordance with various aspects of the present invention.

The outer diameter of the elongate tube 11 portion of the sample tube 10 can be varied depending on desired use and application. The outer diameter of the elongate tube 11 can be the same or different from the outer diameter of the gripping section 16. Thus, the gripping section 16 can be sized to cooperatively interact with a laboratory automation system while the elongate tube 11 can be sized for different sample or instrument requirements. One or more embodiments of sample tube 10 have an elongate tube 11 with a diameter in the range of about 0.77 mm to about 25 mm. In specific embodiments, the elongate tube 11 has a diameter of about 0.77 mm, 1.0 mm, 1.4 mm, 1.7 mm, 2 mm, 2.5 mm, 3 mm, 4 mm, 4.25 mm, 5 mm, 6 mm, 8 mm, 10 mm, 12 mm, 15 mm, 20 mm or 25 mm.

The inner diameter of the elongate tube 11 can be constructed depending on instrument and sample needs. Varying the inner diameter of the elongate tube 11 allows for the sample tube wall thickness to be controlled, as different instruments and laboratory automation systems require sample tubes with different wall thicknesses. In detailed embodiments, the sample tube 10 has a constricted configuration which allows for, inter alia, decreased sample volumes.

The actual dimensions of normal (usually referred to as thin wall), medium or heavy wall thicknesses depends greatly on the outside diameter of the sample tube. What would be considered a heavy wall thickness for a 1 mm diameter tube would be completely inappropriate, for example, for a 5 mm diameter tube because the wall would be very thin and fragile and prone to breakage. For example, a normal or thin wall thickness for a 1 mm outside diameter tube is about 0.10 mm (about 0.004 in), a medium wall thickness is about 0.14 mm (about 0.005 in) and a heavy wall thickness is about 0.21 mm (about 0.008 in). For a 5 mm outside diameter tube, which is the most commonly used size, a normal or thin wall thickness is about 0.40 mm (about 0.016 in), a medium wall thickness is about 0.80 mm (about 0.031 in) and a heavy wall thickness is about 1.40 mm (about 0.055 in).

The sample tube length can be varied depending on desired use and application, as different instruments and laboratory automation systems require tubes of different lengths. In one or more embodiments, the sample tube 10 has a length in the range of about 4 inches (about 100 mm) to about 16 inches (about 406 mm). In specific embodiments, the sample tube 10 has a length of about 4 inches (about 100 mm), about 4.075 inches (about 103.5 mm), about 7 inches (about 178 mm), about 8 inches (about 203 mm), about 9 inches (about 229 mm) about 9.8 inches (about 250 mm), about 14 inches (about 356 mm) or about 16 inches (about 406 mm).

Sample tube runout (also called camber) can range from a low of about 0.00002 inch per 1 inch tube length (about 0.0005 mm per 25.4 mm of tube length) to a high of about 0.0005 inch per 1 inch of tube length (about 0.013 mm per 25.4 mm of tube length). These examples are specific values for different grades or quality of sample tubes and should not be considered as limiting values because camber values are usually higher, though not routinely measured, for lower grades of sample tubes such as economy or disposable grades. Additionally, because many newer NMR instruments are capable of routinely performing non-spinning experiments, camber can range to higher values than specified, to as much as about 0.003 inches per inch of tube length (about 0.076 mm per 25.4 mm of tube length) or even higher. Conversely, camber values can also be virtually zero for high quality tubes. The low value quoted above is the maximum allowable camber for a high quality tube, but does not preclude a lower value. In specific embodiments, the sample tube has a camber less than about 0.005 inches, 0.004 inches, 0.003 inches, 0.002 inches, 0.001 inches, 0.0005 inches, 0.00025 inches, 0.0002 inches, 0.0001 inches, 0.00005 inches, 0.000025 inches, 0.00002 inches or 0.00001 inches per inch of tube length.

Figure 4:
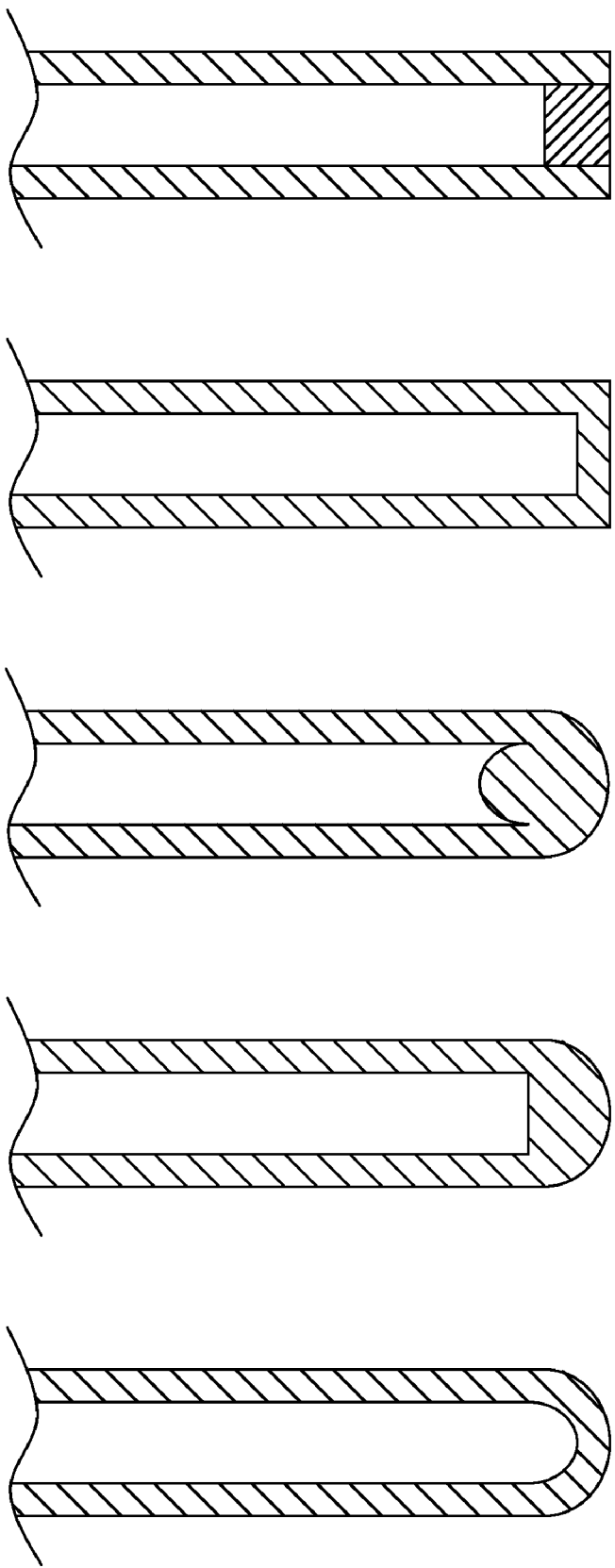
FIG. 4 shows cross-sectional views of bottom closures in accordance with one or more embodiments of the present invention.

The closed end 15 of the sample tube 10 can be closed (or sealed) by any suitable technique. Non-limiting examples of suitable techniques include, heat fusing the end of the elongate tube 11, inserting a plug into the end of the elongate tube 11 and heating to fuse or applying an adhesive to seal the end. FIG. 4 shows several examples of sample tubes 10 various closed ends. FIG. 4A shows an end with roughly uniform wall thickness as the elongate tube. This type of closed end can be formed by, for example, heat sealing, machining, or molding processes. FIG. 4B shows a sample tube with a squared off end which can be formed by, for example, heat sealing the tube, machining or by molding processes. The end piece of FIG. 4B can also be a plug that is attached to the end of the tube by heating or an adhesive. FIG. 4C shows a sample tube with an end inverse to that of FIG. 4A. This type of end can be formed by heat sealing to insertion of a spherical plug into the sample tube and sealing with heat or an adhesive. FIG. 4D shows a flat ended tube which can be formed in the same fashion as that of FIG. 4B. FIG. 4E shows a flat ended tube that is sealed with a plug made of a different material than the elongate tube. In this detailed embodiment, the plug is not integrally formed with the elongate tube. This plug can be sealed in place by, for example, application of heat or an adhesive material. In specific embodiments, the plug forms a fluid tight seal with the inside surface of the elongate tube by one or more of a friction fit, heat fusing or an adhesive. The tube ends shown in FIG. 4 are merely illustrative and should not be taken as limiting the scope of the invention.

In detailed embodiments, the closed end 15 is formed by heating the material of the tube until it softens, at which point the material can be closed in upon itself to form a hermetically sealed liquid tight closure. The heating may be accomplished by an oxygen/fuel gas flame, but other suitable methods, such as by means of an electrically heated resistance wire or coil, ultrasonic or radiofrequency heating or laser heating.

In some specific embodiments, the closure can also be formed by inserting a closely matching solid cylindrical plug of material into one end of the tube. The plug can be retained in place by a friction or press fit, or it can be heated to fuse the plug to the cylindrical wall of the tube, or it can be cemented or glued in place by means of an adhesive.

Additional aspects of the invention are directed to methods of making a sample tube 10. Referring again to FIG. 1, a cylindrical elongate tube 11 is formed. The elongate tube 11 has an inside surface 12, an outside surface 13 and two ends 14 and 15. A first end 15 of the cylindrical elongate tube 11 is closed to form a tube having a closed first end 15 and an open second end 14. At least one discontinuity 17 is formed along a gripping region 16 located adjacent the open second end 14 of the elongate tube 11.

The gripping section 16 (also referred to as a "gripping region"), including discontinuities 17, can be formed substantially simultaneously with the elongate tube 11. As used in this specification and the appended claims, the term "substantially simultaneously" means that the features are formed within the same processing step. For example, during an injection molding process.

In detailed embodiments, the closed end 15 of the cylindrical elongate tube 11 is integrally formed with the elongate tube 11. This means, for example, that the material used to seal the closed end 15 is the material of the elongate tube 11. In specific embodiments, the closed first end 15 of the elongate tube 11 is closed by one or more of heat sealing or plugging the first end 15 of the elongate tube 11.

In detailed embodiments, the at least one discontinuity 17 in the gripping region 16 is formed by a machining process.

Molding

Molding is generally understood to refer to a process whereby molten material, such as glass or a polymer such as fluorinated ethylene-propylene (FEP) polymer is poured or forced into a cavity. The cavity is formed inside of a block of a suitable material, and the cavity reproduces the outside shape and dimensions of the object to be molded, in this case being the sample tube, including the desired grooves and/or ribs near the open end. The mold can also incorporate features to reproduce the inside shape and dimensions of the object to be molded. For the sample tube this can be accomplished by, for example, a pin that projects into the mold cavity, thereby shaping the inside contour of the tube.

Air pressure can also sometimes be used in place of the pin to shape the inside of the tube. The air pressure forces a bubble of the molten material into the mold cavity, causing the bubble of the molten material to conform to the shape of the mold cavity and leaving a void in the interior of the tube. Molding usually produces the desired object in its entirety, with no further operations necessary.

Tooling

Tooling is generally understood to refer to a process whereby an already formed object is further shaped while in a semi-molten state. In the case of the sample tube, tooling can be employed to form the desired diameter, grooves and/or ribs near the open end of the tube, the bottom closure of the tube already having been formed as described previously. Tooling is usually accomplished using a handheld device that is manually clamped or closed over the tube or other object to be tooled, while the object is being rotated in a lathe, and having been heated sufficiently in the area to be tooled so that the object, or tube, is in a sufficiently soft or semi-molten state to allow the softened material to flow and conform to the inside shape of the tool. Tooling is usually performed on glass, but can be applied to other materials, such as a polymer, including the fluorinated polymers mentioned previously.

Figure 5:
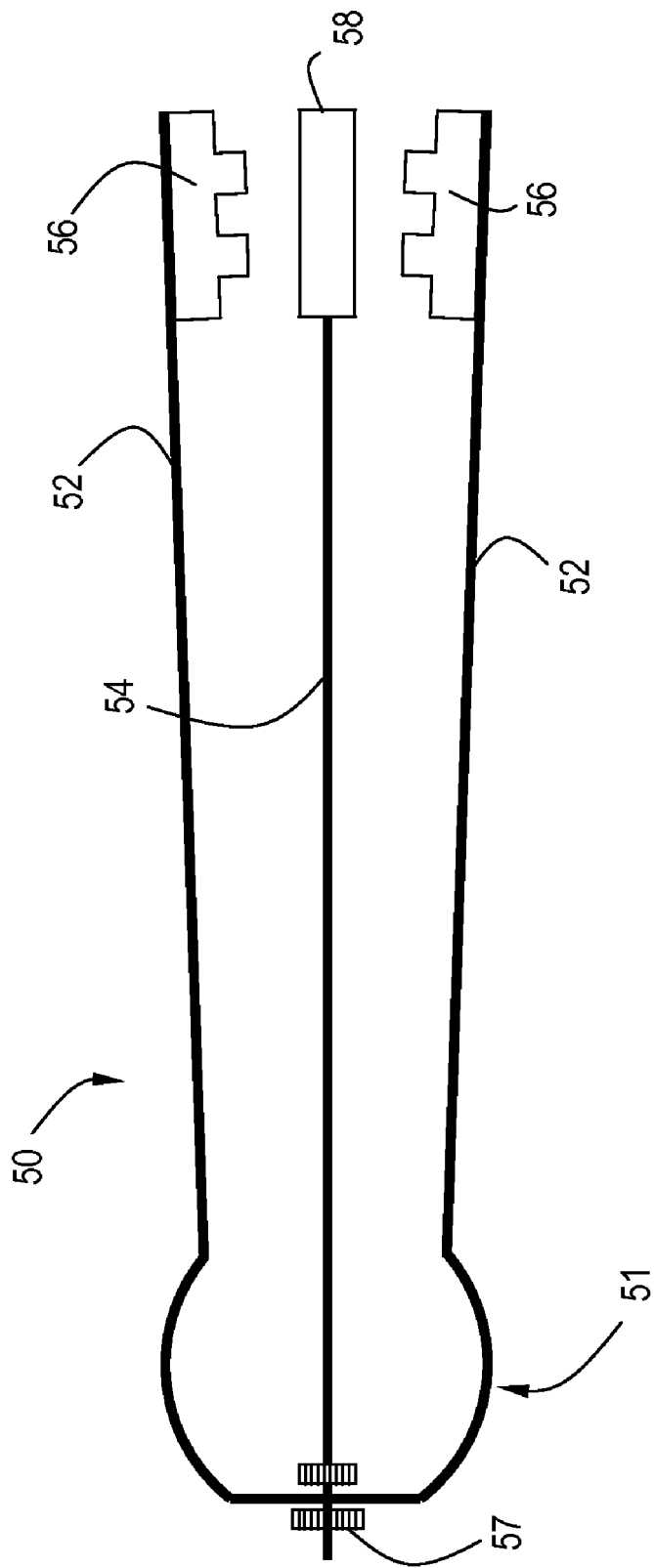
FIG. 5 shows a cross-sectional view of a handheld tool for tooling a gripping region of an elongate tube in accordance with one or more embodiments of the present invention.

In some detailed embodiments, the at least one discontinuity 17 is formed in the gripping region 16 by tooling the second open end 14 of the elongate tube 11 using a discontinuity tool. FIG. 5 shows an example discontinuity tool 50 for use with one or more embodiments of the invention. The discontinuity tool 50 includes a central hub 51 with at least one jaw arm 52 and a pin arm 54. The central hub 51 may include a screw connector 57 which enables the discontinuity tool 50 to be disassembled. The discontinuity tool 50 comprises a pin 58 attached to the pin arm 54. The pin 58 shaped to tool the inner surface 12 of the elongate tube 11 to produce a desired shape. The discontinuity tool 50 also comprises at least one jaw 56 for tooling the outside surface 13 of the elongate tube 11. The discontinuity tool 50 shown in FIG. 5 would be useful in creating the sample tube 10 shown in FIG. 1.

The tool is generally made from steel or stainless steel, or any other suitable metal or material that can withstand the heat and corrosive effects experienced during the tooling process. The tool often consists of a spring loaded or spring metal handle, much like a pair of tongs, with two matching halves or jaws that are attached to the ends of the handle. The jaws are shaped on the inside surfaces to reproduce the outside shape and dimensions of the object to be tooled. When the handle is squeezed closed the two jaws meet in close alignment, thereby reproducing the outside shape and dimensions of the object to be tooled. There is usually also a third element, which is attached to a centrally located shaft in such a way so that this third element extends into the center of the two jaws when the jaws are closed together. The third centrally mounted element reproduces the inside shape and dimensions of the object to be tooled.

The tooling process is usually performed on a lathe, but can employ any mechanism or machine that rotates the object to be tooled, so that heat can be applied evenly around the area to be tooled. After the object has been sufficiently heated, the tool described above is closed down upon the object while it is still being rotated, thereby effecting the tooling operation. An oxygen/fuel gas flame is the usual source of heat, but other sources can be used, such as an electrically heated resistance wire or coil, ultrasonic or radiofrequency heating and laser heating. Additionally, a lubricant is usually applied to the tool before the tooling process. In detailed embodiments, when tooling glass, a suspension of colloidal graphite in water, or the like, is used as a lubricant.

Machining

Machining is generally understood to be a process whereby a rotating cutting tool is brought into contact with the object to be machined, which is usually also rotating, in a machine such as a lathe. In some instances, the object to be machined is stationary, with only the cutting tool rotating, as is the usual case when using a milling machine or grinder. In other cases, only the object to be machined is rotating, with the cutting tool being stationary, such as when drilling a hole using a drill in a lathe. In any case, machining removes material from the object being machined by various physical processes such as abrasion or shear. For the sample tubes, machining processes would most often be employed to fashion the grooves and/or ribs near the open end of the tube, with the bottom closure having already been formed as described previously.

In the case of machining the glass sample tubes, abrasion or grinding processes are usually employed, using abrasive wheels or discs made of, for example, silicon carbide, aluminum oxide or diamond impregnated or coated wheels, discs and drills. For machining other materials, such as a polymer, including the fluorinated polymers like polytetrafluoroethylene (PTFE), standard cutting tools such as end mills, lathe tool bits and drills made from carbon steel, high speed steel or tungsten carbide can be used.

Because machining processes can only remove material rather than reshaping the existing material, the shape and physical dimensions of the object to be machined must be sufficiently large to accommodate the required finished shape. In the case of the sample tubes, it may often be necessary to start with a piece of material that has a larger diameter than the outside diameter of the sample tube. This larger diameter piece of material can be fashioned into, for example, a sleeve or hollow tube that fits closely over the outside diameter of the sample tube. The sleeve can then be secured into place on the sample tube by fusing the two together with heat, by a friction or press fit or by using an adhesive bonding material. Especially for the smaller diameter sample tubes, the larger diameter sleeve can be machined to match the nominal design diameter, as described previously, of the robotic fingers or rounded robotic grippers used on the automated sample handling systems. In the same process, the required grooves and/or ribs can be machined into the larger diameter sleeve as well.

Figure 6:
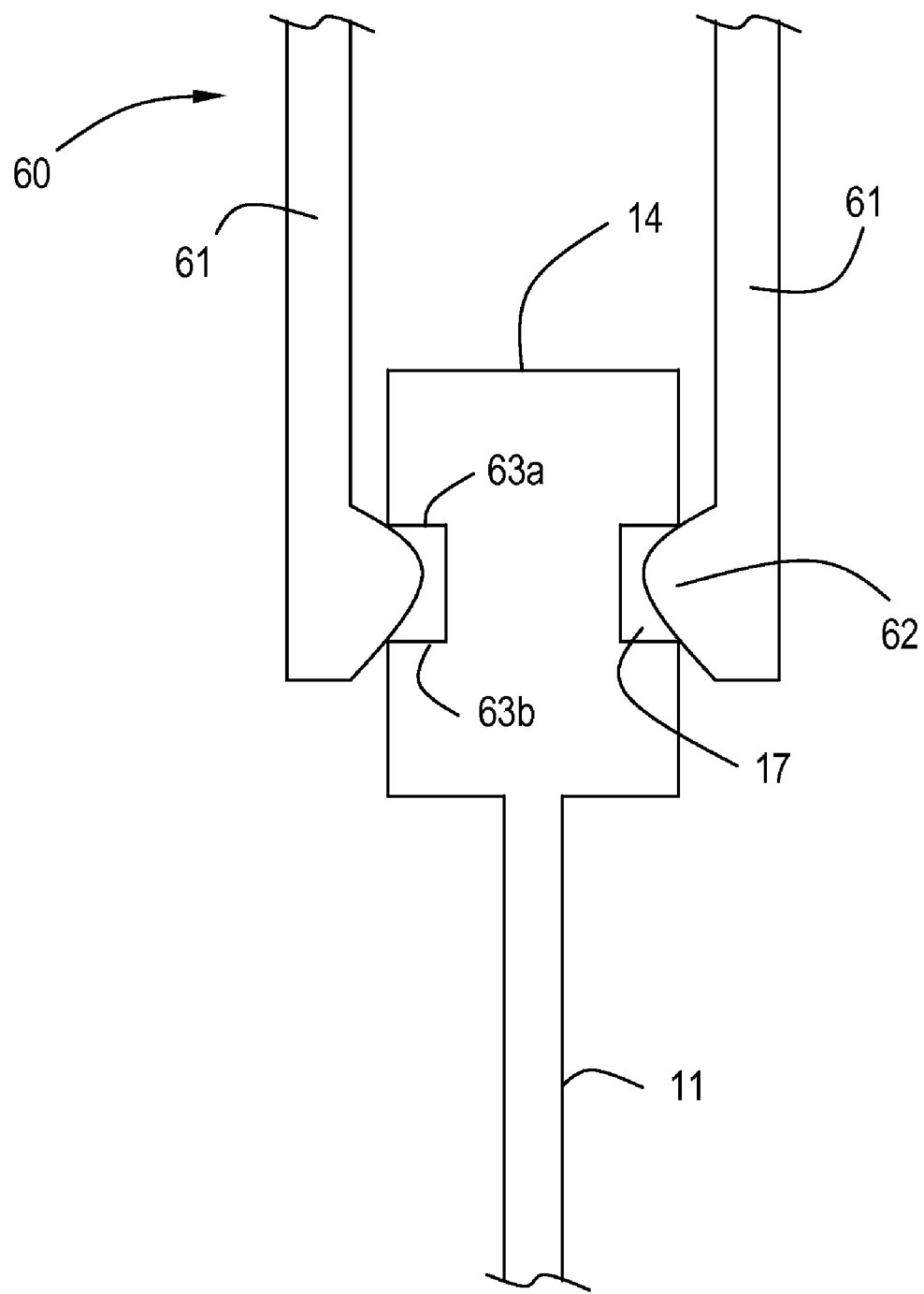
FIG. 6 shows a cross-sectional view of a sample tube being held by the gripping fingers of a sample handler.

Additional aspects of the invention are directed to methods of using a sample tube 10 in a sample handler. With reference to FIG. 6, the sample tube 10 has an open end 14 and a closed end (not shown) and one or more discontinuities 17 near the open end 14. The sample handler includes a gripping device 60 with a plurality of gripping fingers 61 adapted to safely contact the sample tube 10. The closed end of the sample tube 10 can be placed in a holder (not shown) in the sample handler. The gripping device 60 can be lowered over the open end 14 of the sample tube 10 so that the gripping fingers 61 can cooperatively interact with the at least one discontinuity 17 on the sample tube 10. The sample tube 10 can be lifted by moving the gripping fingers 61 to remove the sample tube from the sample handler.

In specific sample handlers, the gripping fingers 61 have a projection 62 which presses onto two outer edges 63a, 63b of the at least one discontinuity 17. This enables the gripping device 60 to safely move the sample tube 10 in the vertical or horizontal axes while maintaining a solid grip on the sample tube.

Suitable sample handlers include, but are not limited to, Bruker Biospin SampleJet and Match systems, Varian automated sampling systems, and automated sample preparation systems. In specific embodiments, the gripping device 60 is a Bruker Biospin SampleJet system.

Detailed embodiments include capping the open end 14 of the sample tube 10 with a suitable cap.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

The invention claimed is:

1. A sample tube comprising a cylindrical elongate tube having an inside surface, an outside surface, an open end, a closed end and a gripping section adjacent the open end, the gripping section having at least two discontinuities extending about the outside surface of the elongate tube,
wherein the elongate tube has a camber up to about 0.005 inch per inch of tube length.

2. The sample tube of claim 1, wherein each of the discontinuities is one of a projection and a recess.

3. The sample tube of claim 1, wherein there are three discontinuities in the gripping section of the elongate tube.

4. The sample tube of claim 1, wherein the elongate tube is constructed from a material selected from the group consisting of borosilicate glass, soda lime glass, flint glass, polytetrafluoroethylene (PTFE), fluorinated ethylene-propylene (FEP) polymer and perfluoroalkoxy (PFA) polymer.

5. The sample tube of claim 1, wherein the gripping section is integrally formed with the cylindrical elongate tube.

6. The sample tube of claim 1, wherein the gripping section comprises a sleeve not integrally formed with the elongate tube secured to the sample tube.

7. The sample tube of claim 1, wherein the elongate tube has a diameter in the range of about 0.77 mm to about 25 mm.

8. The sample tube of claim 1, wherein the sample tube has a length in the range of about 4 inches to about 16 inches.

9. The sample tube of claim 1, wherein the closed end of the cylindrical elongate tube is integrally formed with the elongate tube.

10. The sample tube of claim 1, wherein the closed end of the cylindrical elongate tube comprises a plug not integrally formed with the elongate tube.

11. The sample tube of claim 10, wherein the plug forms a fluid tight seal with the inside surface of the elongate tube by one or more of a friction fit, heat fusing or an adhesive.

12. The sample tube of claim 1, wherein the gripping section has a larger outer diameter than the elongate tube.

13. The sample tube of claim 1, wherein the gripping section has a smaller outer diameter than the elongate tube.

14. The sample tube of claim 1, wherein the at least two discontinuities in the gripping section are formed by one or more of molding, tooling and machining processes.

15. A method of using a sample tube in a sample handler, the sample tube having an open end, a closed end and one or more discontinuities near the open end, the method comprising:
placing the closed end of the sample tube in a holder in the sample handler;
moving a gripping device to the open end of the sample tube so that the gripping device cooperatively interacts with the one or more discontinuities in the sample tube; and
lifting the gripping device and the sample tube out of the sample handler.

16. The method of claim 15, further comprising capping the open end of the sample tube.

* * * * *